(12) United States Patent
Chen et al.

(10) Patent No.: US 9,610,054 B2
(45) Date of Patent: Apr. 4, 2017

(54) AUTOMATIC SCANNING AND POSITIONING APPARATUS FOR A SCOUT IMAGE

(71) Applicant: GE MEDICAL SYSTEMS GLOBAL TECHNOLOGY COMPANY LLC, Waukesha, WI (US)

(72) Inventors: Yusi Chen, Sichuan (CN); Yilun Shi, Beijing (CN); Ping Liu, Beijing (CN); Ying Li, Beijing (CN)

(73) Assignee: General Electric Company, Schenectady, NY (US)

( * ) Notice: Subject to any disclaimer, the term of this patent is extended or adjusted under 35 U.S.C. 154(b) by 469 days.

(21) Appl. No.: 14/138,163

(22) Filed: Dec. 23, 2013

(65) Prior Publication Data

US 2014/0185740 A1 Jul. 3, 2014

(30) Foreign Application Priority Data

Dec. 28, 2012 (CN) .......................... 2012 1 0586793

(51) Int. Cl.
*A61B 6/03* (2006.01)
*A61B 6/00* (2006.01)

(52) U.S. Cl.
CPC .............. *A61B 6/488* (2013.01); *A61B 6/501* (2013.01); *A61B 6/545* (2013.01); *A61B 6/032* (2013.01)

(58) Field of Classification Search
CPC ........... A61B 6/488; A61B 6/501; A61B 6/52; A61B 6/545; A61B 6/032
See application file for complete search history.

(56) References Cited

U.S. PATENT DOCUMENTS

| | | | |
|---|---|---|---|
| 2007/0116337 A1* | 5/2007 | Toth ....................... | A61B 6/032 382/128 |
| 2008/0159611 A1* | 7/2008 | Tao ........................ | A61B 6/488 382/131 |

FOREIGN PATENT DOCUMENTS

| CN | 101234028 A | 8/2008 |
|---|---|---|
| CN | 102342847 A | 2/2012 |
| CN | 102365655 A | 2/2012 |

* cited by examiner

*Primary Examiner* — Glen Kao

(57) ABSTRACT

An automatic scanning and positioning apparatus for a scout image, comprising: a receiving means, for receiving a scout image of a subject obtained through scout scanning; a checking and determining means, for automatically checking at least one position in the scout image according to a plurality of information contained in the scout image, and automatically determining a scanning scope based on the at least one position; and an executing means, for executing axial scanning to the subject based on the determined scanning scope.

13 Claims, 4 Drawing Sheets

AUTOMATIC SCANNING AND POSITIONING APPARATUS FOR A SCOUT IMAGE

TECHNICAL FIELD

The present invention generally relates to a scanning and positioning apparatus in the medical field, more particularly, relates to an automatic CT scanning and positioning apparatus for human face scout image.

BACKGROUND OF THE INVENTION

Sinuses scan in hospitals are mainly used for diagnosing injury, deformity, malignant tumor and inflammation. A doctor firstly scans a scout image so as to localize the position of sinuses from a frontal sinus to a nose (including external nose, nasal cavity). Currently the above positioning is a manual operation completed by the doctor. The doctor needs to manually click or drag a mouse to change the start position and end position of the final axial scanning on the scout image. There exist a lot of defects in the manual positioning of sinuses scan.

On the other hand, orbit scan in the hospitals are mainly used for the diagnosis of orbital structural diseases and orbital components, injuries and foreign objects. The doctor also needs to scan a scout image, so as to position the orbit from 0.5 cm below the eyehole to 0.5 cm above the eyehole through manual operations. The doctor needs to manually click or drag a mouse to change the start position and end position of the final axial scanning on the scout image. There exist a lot of defects in the manual positioning of orbit scan.

FIG. 1 shows in more details a flow chart 100 of manually positioning a scout image in the prior art. At starting Step 102 of the flow, a patient such as a subject is positioned at a position convenient for being scanned, e.g., the patient is usually transported and positioned at a stand of a scanning system. Then, at Step 104, scout scanning is conducted to the patient, so as to obtain a scout image. As a non-restrictive example of the above step, the scout image can be obtained by adopting the following manner: an operation console in a X-ray CT apparatus is utilized to control a scanning frame of the X-ray CT apparatus, such that a X-ray tube in the scanning frame emits X-rays (the X-rays, e.g., are shaped through pores to be represented as fan-shaped beams, cone-shaped beams, etc.); the shaped X-rays are transmitted towards the patient positioned on the stand, penetrate through the patient and are applied to a X-ray detector (the detector can be X-ray detecting elements having a plurality of two dimensional settings in the propagation direction (channel direction) and thickness direction (column direction) of the fan-shaped X-ray beams) of the X-ray CT apparatus located on another side of the stand; finally, a data acquisition segment of the X-ray CT apparatus acquires detected data from various X-ray detecting elements, take the data as projection data, and obtains a "scout image" based on the projection data. Incidentally, the image per se indicating the scout image and the image data bearing the image all can be called scout image in the whole text, without any distinction.

Next, at Step 106, a user (e.g., a doctor) manually adjusts and positions the scout image generated at Step 104 based on his/her own experiences and vision. Then, at Step 108, he/she manually sets a final axial scanning scope on the scout image, e.g., manually clicking or dragging a mouse to set, change, adjust the start position and end position of the axial scanning. In other situations, the user can also make changes and adjustments to the scanning scope (e.g., the start position and end position) through keyboard input, voice input, or other known ways. Finally, at Step 110, the user confirms the adjusted scout image and scanning scope by clicking a confirmation button on a graphical user interface (not shown), and performs the axial scanning (e.g., CT tomography scan) based on the scanning scope, so as to form an axial scanning image for further treatment or diagnosis.

The currently known defects existing in the above manual positioning 100 of scout image (e.g., sinuses scan and orbit scan) include, but are not limited to: the manual positioning 100 takes time and efforts; it mainly relies on the doctor's experiences and vision; and in the case that the operator is not familiar enough with it, the manual positioning 100 may be inaccurate, and thus is unable to execute the anticipated axial scanning. Further, since the eyes of the subject are usually sensitive to X-rays and it is hoped that the least radiation dose is incident into the eyes, it is extraordinarily desired in the art that orbital scanning is automatically positioned with high precision.

In this field, there are already some ways and means, for positioning scanning images.

For example, a Chinese patent application (CN 101234028A), published on Aug. 6, 2008, presents a method of generating a CT scanning scout image in a SPECT-CT based multiple mode scanning system. The method utilizes image information (e.g., loid) of the SPECT side to fill in the scan option of a scan protocol of the CT side, and utilizes the filled scan protocol to read out SPECT image at the CT side to act as scout image at the CT side. However, the above method focuses on the compensation of SPECT mode to CT mode, thereby realizing less dose and higher availability, but fails to solve the technical problem of automatically positioning scout image which is anticipated by this disclosure to be solved.

As another example, a Chinese patent application (CN 102365655A), published on Feb. 29, 2012, presents an image matching device based on an ICP (Iterative Closest Point) method, in which a solution is converged to an optimal solution while avoiding the ICP method to reach a local solution (i.e., only ensuring the error function to reach the local minimal value). However, this patent application does not relate to the apparatus of automatically positioning scout image as depicted by the present disclosure.

As a further example, a Chinese patent application (CN 102342847A), published on Feb. 8, 2012, presents realizing a scan range in which unnecessary exposure to a subject 8 is reduced, by simultaneously adjusting a tilt angle of a tilt image to be reconstructed and a tilt image reconstruction range (via a tilt image reconstruction range input reception unit 602) and adjusting a scan range for a non-tilt scan (via a non-tilt scan range input unit 603). However, adjustments to the tilt image reconstruction range and the scan range for a non-tilt scan still need to manually conducted, so the problem anticipated by the present disclosure to be solved cannot be solved by the above application.

In summary, in the prior art, there exists no automatic positioning apparatus for scout image scan (e.g., sinuses scan and orbit scan as mentioned above) with high precision. Therefore, an apparatus for efficiently automatically positioning scout scan such as sinuses scan and orbit scan, is desired.

BRIEF SUMMARY OF THE INVENTION

In order to solve the above and other technical problems, an automatic scanning and positioning apparatus for a scout image, is provided.

According to one aspect, Here is presented an automatic scanning and positioning apparatus for a scout image, comprising: a receiving means, for receiving a scout image of a subject obtained through scout scanning; a checking and determining means, for automatically checking at least one position in the scout image according to a plurality of information contained in the scout image, and automatically determining a scanning scope based on the at least one position; and an executing means, for executing axial scanning to the subject based on the determined scanning scope.

Utilizing the automatic scanning and positioning apparatus mentioned herein, can save time, increase imaging speed, and further obtain higher image throughput within a given time and avoid excessive manpower consumption. Compared with the manual positioning in the prior art, the automatic scanning and positioning apparatus disclosed herein uses a multiple information fuzzy algorithm, thereby being more accurate, having better imaging performance, and give a clinician a better user experience.

In addition, the automatic scanning and positioning apparatus disclosed herein, when applied in orbit scanning, further has the following additional advantage: reducing the radiation dose of X-rays, thereby avoiding potential damage to human eyes.

BRIEF DESCRIPTION OF THE DRAWINGS

When referring to the drawings and reading the detailed depiction below, these and other features, aspects and advantages will be better understood, and in all the drawings, similar reference signs denote similar parts, in which drawings.

DETAILED DESCRIPTION OF THE INVENTION

One or more embodiments of the present technique will be depicted below. In order to try to provide a concise depiction of these embodiments, the present description does not depict all features of real implementation. It should be aware that in the development of any such real implementation, during any engineering project or design project, manifold decisions for realizing specifics must be made so as to achieve specific goals of developers, e.g., to be consistent with system-related and business-related constraints, which may vary depending on different implementations. Furthermore, it should be aware that, for persons skilled in the art who are benefit from this disclosure, such a development achievement may be complicated and time consuming, but in spite of such, is still a routine in design, manufacture and process.

An element or step as used herein which is quoted in a singular form and follows an indefinite article "a/an", shall be construed as not excluding multiple elements or steps, unless such exclusion is clearly stated. In addition, the quotation "one embodiment" disclosed herein does not intend to be interpreted as excluding the presence of additional embodiments which also combine the features as quoted. In addition, unless clearly stated otherwise, an embodiment "comprising" or "having" element or element having a specific property may include additional elements having not this property.

Figure 1:
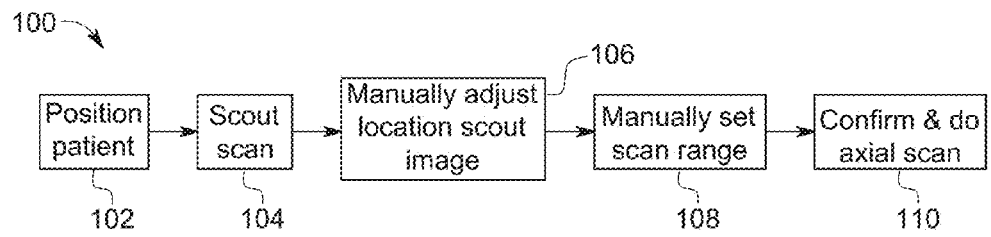
FIG. 1 is a principle block diagram of manually positioning a scout image in the prior art.
Figure 2A:
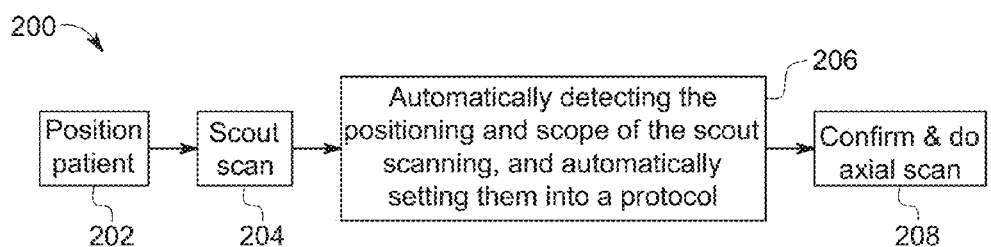
FIGS. 2A, 2B, and 2C are principle block diagrams of automatically positioning scout scan as disclosed herein, wherein the scout scan includes, e.g., sinuses scan and orbit scan.

According to one embodiment as disclosed herein and referring to FIG. 2A, in order to improve the flow 100 (see FIG. 1) of manually positioning a scout image, the present disclosure proposes a method 200 of automatically positioning scout scanning, which method is realized by adopting corresponding devices. The preceding Steps 202 and 204 of the method 200 of automatically positioning scout scanning are similar to Step 102 and Step 104 as depicted above by combining FIG. 1, and can be realized by adopting the same existing technical devices, so no repetitive depiction will be made herein. That is, through a manner similar to Steps 102 and 104, a scout image of a subject, such as an anteroposterior (AP) scout image, can be obtained herein.

Next, at Step 206, the method disclosed herein utilizing a receiving means (not shown) such as a receiver to receive the scout image of the subject; and adopting a means such as a processer to automatically check at least one position (in an embodiment, sinuses or orbit) in the scout image according to a plurality of information contained in the scout image, and to automatically determine the scanning scope based on the at least position. Persons skilled in the art will appreciate that, the determined scanning scope can be further automatically set into the currently used scanning protocol, for further treatment.

Finally, at Step 208, the operator confirms whether the scanning scope is reasonably set via a graphical user interface (not shown), and in a reasonable case, starts up an axial scanning to obtain the desired CT image. Persons skilled in the art will appreciate that, after the method 200 is completed, the obtained axial scanning image can be output via an output means (e.g., a display, a printer, etc.), and can also be stored in a memory for future use.

Figure 2B:
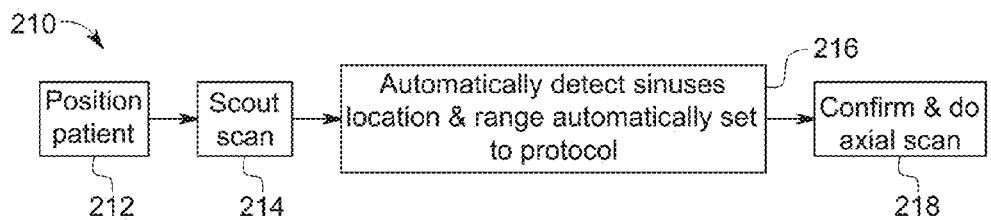

According to one embodiment, FIG. 2B depicts a principle block diagram 210 of automatically positioning scout scan, wherein the scout scan is a scan to "sinuses" of human face. In the automatic positioning 210 of scout scan, Steps 212, 214 and 218 correspond to Steps 202, 204 and 208 as depicted above by combining FIG. 2A, and the only difference lies in that Step 216 is directed against sinuses scan, which will be explained below in more details by combining FIGS. 3B-3D and FIG. 4.

Figure 3A:
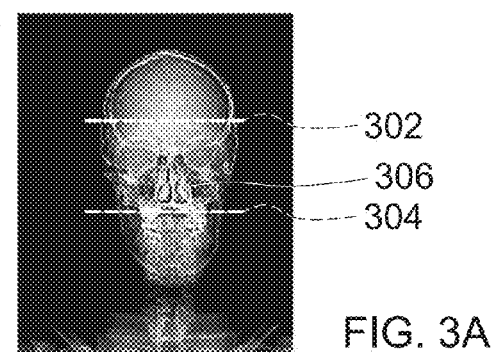
FIG. 3A describes a schematic diagram of manually landmarking the scope of sinuses scan in clinical application.
Figure 3B:
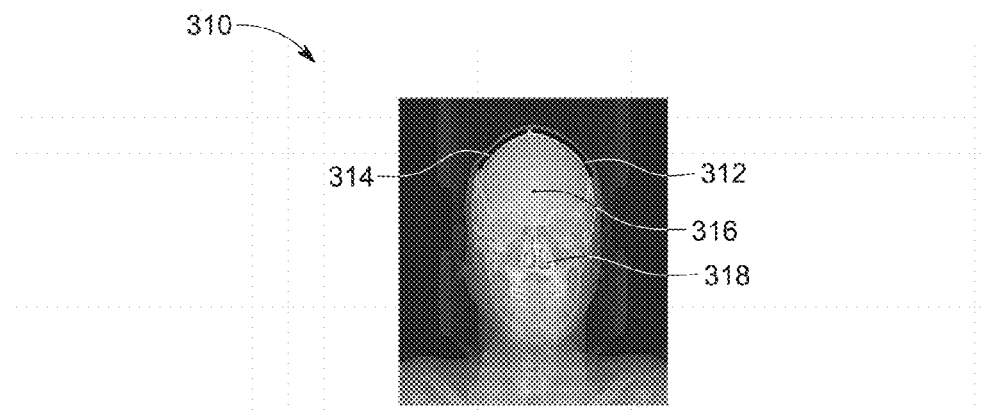
FIGS. 3B,3C, and 3D depict in more details a process of automatically positioning sinuses scan as disclosed herein.
Figure 3C:
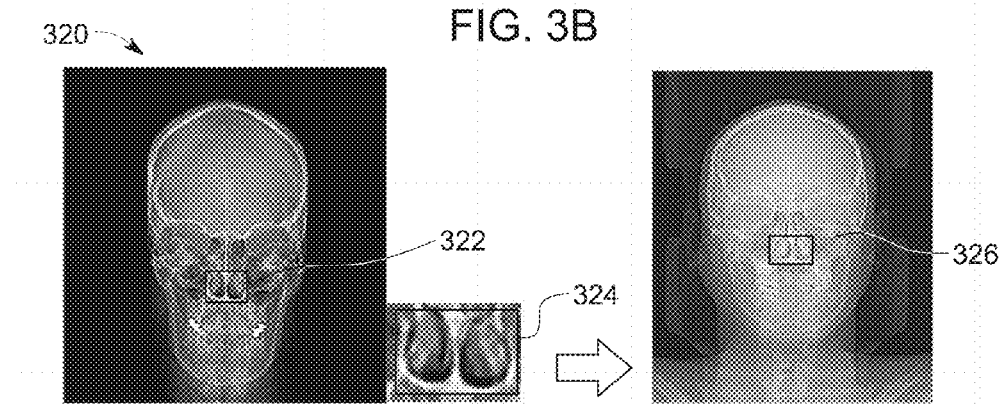

Before Step 216 is explained in details, firstly FIG. 3A is combined to briefly depict how to manually landmark the sinuses scanning scope in the current clinical applications. As shown in FIG. 3A, an AP scout image 300 can be obtained via scout scanning treatment; subsequently when sinuses scanning is needed, the clinician landmarks the frontal sinus horizontal line 302 and the nasal end horizontal line 304 of human face on the image 300 based on his/her own experiences, and determines sinuses 306 to be scanned between the two lines. Selection of the above sinuses sites 306 is illustrative, and according to different needs, sinuses sites at other positions within the scope of the frontal sinus and the nasal end can be selected.

Figure 3D:
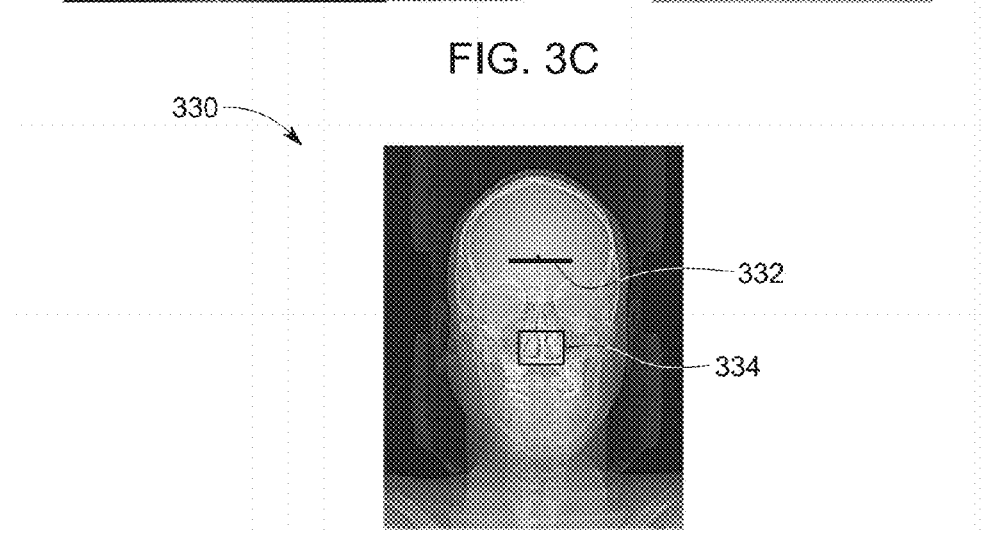
Figure 4:
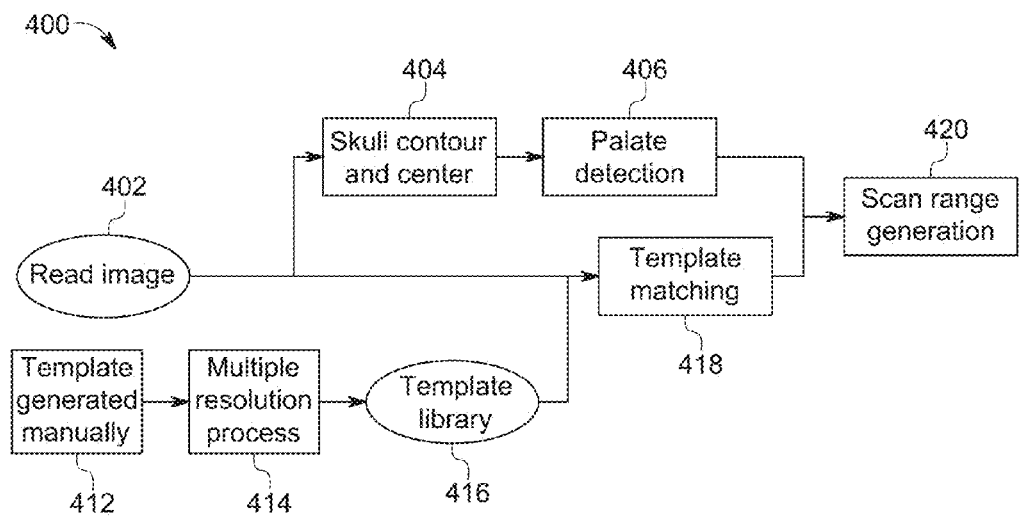
FIG. 4 schematically shows a principle block diagram of a sinuses detecting algorithm as disclosed herein.

In the sinuses detecting algorithm 400 as shown in FIG. 4, in order to automatically position sinuses scanning, firstly the frontal sinus needs to be positioned according to information contained in the scout image, and then the scanning scope is automatically obtained according to template matching. To be specific, the algorithm 400 begins at Step 402, in which the scout image is read. Then, at Step 404, the frontal sinus detecting module (not shown) can conducts circular fitting based on gradient information and grayscale information of skull contained in the scout image (see FIG. 3B), thereby obtaining position information of skull contours 312, 314 and skull central point 316. Since the central point of skull is close to the frontal sinus of human face, it can be selected as a reference point for frontal sinus detection. Next, at step 406, the frontal sinus detecting module automatically determines the final position of the frontal sinus based on this reference point and using the gradient information and grayscale information of skull as read, e.g., determining whether the frontal sinus has an upper and lower deviation relative to the reference point and determining the width of the front sinus in the horizontal direction, etc. FIG. 3D schematically depicts the frontal sinus detecting result 332, which is located near the skull contour center in the human face schematic diagram 330.

Returning to Step 402, another branch of image information process enters a template matching module 418, in which module image information obtained in Step 402 matches with a multi-resolution template 324 in a template library 416, so as to obtain detection at the nasal (end) position 326. According to one embodiment, the template library 416 is generated based on the previously existing nasal region 412 that is manually landmarked on the anteroposterior scout image; in order to obtain a better recognition effect, the present disclosure also, according to an embodiment, conducts multi-resolution treatment to the manually generated template 412, thereby generating N resolution horizontal images 414, which images constitute the template library 416. Specifically, in the template matching module 418, different search windows 324 corresponding to N resolution horizontal images in the template library 416 are used to conduct correlative matching to image information (e.g., gradient information and grayscale information) obtained in Step 402, and the template that reaches the highest degree of correlation is taken as the best match 326 of the scout image.

How to generate resolution horizontal images and how to adopt correlative matching to find the best math all are commonly known methods in the art, without no unnecessary details provided herein.

Finally, at Step 420, according to the frontal sinus detection 332 obtained by the frontal sinus detecting module and the best match 326 generated in the template matching module 418, a sinuses scanning scope 330 is automatically determined, including the frontal sinus detection 332, and the nasal end scope 334. The sinuses scanning scope can control the final axial scanning directed against sinuses in a manner of being written into a protocol, e.g., can automatically control the start position and end position of the final axial scanning.

Figure 2C:
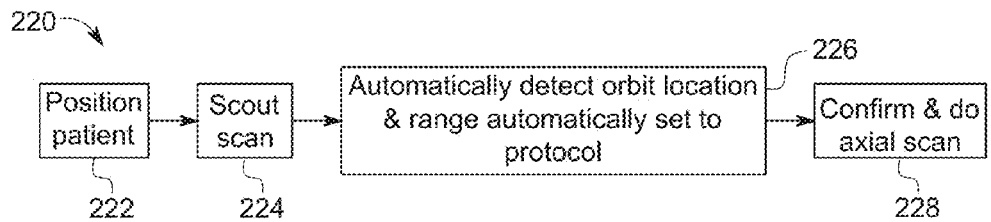

Turning now to FIG. 2C, according to another embodiment, herein is depicted another principle block diagram 220 of automatically positioning scout scan, wherein the scout scan is a scan to "orbit" of human face. In the automatic positioning 220 of scout scan, Steps 222, 224 and 228 correspond to Steps 202, 204 and 208 as depicted above by combining FIG. 2A, and the only difference lies in that Step 226 is directed against orbit scan, which will be explained below in more details by combining FIGS. 5B-5C and FIG. 6.

Figure 5A:
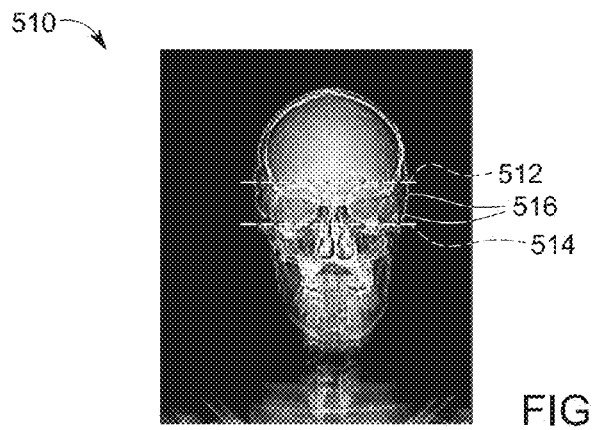
FIG. 5A describes a schematic diagram of manually landmarking the scope of orbit scan in clinical application.

Before Step 226 is explained in details, firstly FIG. 5A is combined to briefly depict how to manually landmark the orbit scanning scope in the current clinical applications. As shown in FIG. 5A, an AP scout image 510 can be obtained via scout scanning treatment; subsequently when orbit scanning is needed, the clinician landmarks orbital boundaries 512 and 514 of human face on the image 510 based on his/her own experiences, and determines orbit 516 to be scanned between the boundaries.

Figure 5B:
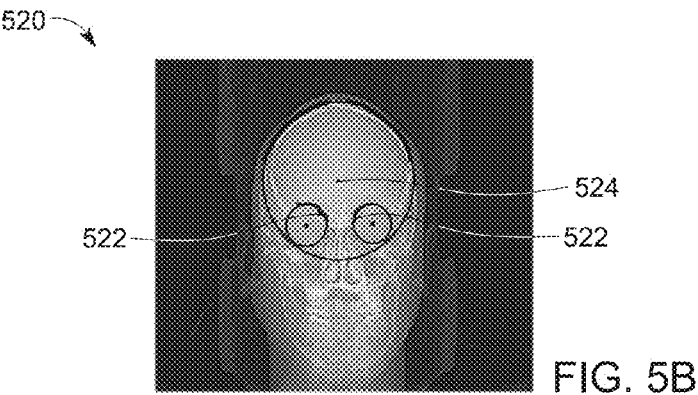
FIGS. 5B-5C depict in more details a process of automatically positioning orbit scan as disclosed herein.
Figure 5C:
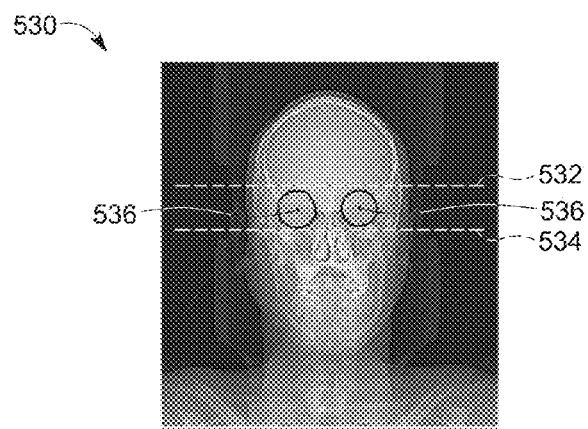
Figure 6:
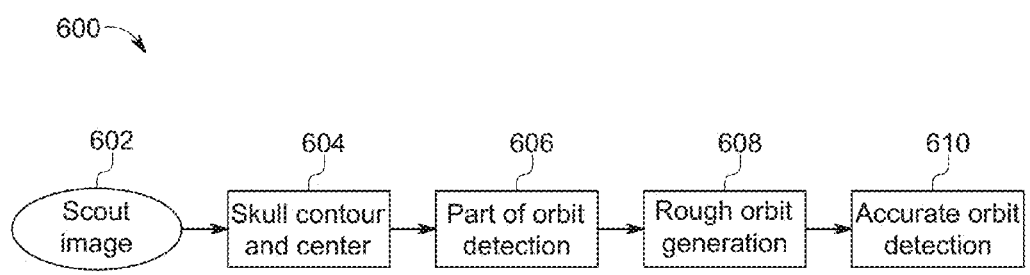
FIG. 6 schematically shows a principle block diagram of a orbit detecting algorithm as disclosed herein.

In the orbit detecting algorithm 600 as shown in FIG. 6, according to one embodiment, in order to automatically determine a orbit scanning scope 530 (see FIG. 5C), firstly a coarse detecting module (not shown) is adopted to position a coarse position of orbit (see FIG. 5B), and then a precise detecting module (not shown) is adopted to position a precise position of orbit (see FIG. 5C). In short, the algorithm 600 begins at Step 602, in which the scout image is read. Then, at Steps 604-608, a coarse detection of orbit is conducted via the coarse detecting module; at Step 610, a precise detection of orbit is conducted via the precise detecting module.

According to one embodiment and referring to 5B, the coarse detecting module uses gradient information and grayscale information of human face image contained in the scout image at Step 602 to obtain position information as a reference. For example, the coarse detecting module can obtain 604 position information of skull contour (further obtaining the radius of skull) and skull central point 524 by adopting the method similar to that as depicted above by combining FIG. 3B. Persons skilled in the art will appreciate that, other position information can also be used by the coarse detecting module as a reference.

Taking the obtained position information as a reference, the coarse detecting module further utilizes such information as gradient information to detect the evident partial contour 522 at the orbital position, thereby further obtaining orbital center and orbital radius. As shown in FIG. 5B, according to the gradient information, only the partial contour 522 of the entire orbit that approaches the neighborhood of the skull central point 524 may be obtained 606. The coarse detecting module can conduct circular fitting based on the partial contour 522 so as to obtain the orbital center (i.e., the centers of two small rounds in FIG. 5B) and orbital radius, thereby generating 608 a coarse orbit.

Next, at Step 610, according to the orbital center and orbital radius at Step 608 and the gradient information at Step 602, by adopting a texture segmentation method, the precise detecting module obtains precision detection 530 of orbit, including orbital boundaries 532 and 534 and orbital approximate position 536, etc. The texture segmentation method is based on different texture features of substances constituting the orbit and substances constituting eyes in the scout image, and precision calculation is conducted on the basis of FIG. 5B, thereby obtaining a relatively precise orbit scanning scope 530 with a relative small amount of calculation. The orbit scanning scope can control the final axial scanning directed against orbit in a manner of being written into a protocol, e.g., can automatically control the start position and end position of the final axial scanning.

The above examples are only several embodiments that illustrate various aspects of the present disclosure, wherein equivalent changes and/or amendments will be readily conceived by persons skilled in the art when reading and understanding the present description and the drawings. Specifically, as for various functions performed by the above components (assemblies, devices, systems, circuits, etc.), unless stated otherwise, the terms (including mentioning "devices") for describing such components intend to correspond to any component such as hardware, software and combination thereof, and to perform the specified function (i.e., being functionally equivalent) of the component, even if it is not structurally equivalent to the structure as disclosed to perform the function in the implementation as shown by the present disclosure. In addition, although specific features of the present disclosure are shown and/or described only against one of several implementations, such features can be combined with one or more other features of other implementations that may be anticipated or favorable to any given or specific application. Moreover, unless stated otherwise, singular component or item as mentioned is expected to comprise two or more such components or items. Furthermore, when the terms "including", "having", "containing", or other variants are used for detailed depiction and/or the claims, such terms intend to denote a meaning of being comprised, and the manner thereof is similar to the term "comprising". Obviously, once the above detailed depiction is read and understood, modifications and amendments will be readily conceived by persons skilled in the art. It is expected that the present disclosure will be construed as including all such modifications and amendments.

The term "processor", as used herein, refers to a central processor, a microprocessor, a microcontroller, a reduced instruction set circuits (RISC), application specific integrated circuits (ASIC), a logic circuit, and any other circuit or processor capable of performing the functions as stated herein.

This written depiction uses examples to disclose the best mode of the present disclosure, and enables persons skilled in the art to practice the present disclosure, including a method of making and using any device or system and performing any combination. The patentable scope that can be obtained by the present disclosure is defined by the claims, and can comprise other illustrative examples that are conceived by persons skilled in the art. If such illustrative examples have the structural elements that are not different from the claims in terms of literal language, or if they include equivalent structural elements that are not substantially different from the claims in terms of literal language, they are specified to fall within the scope of the claims.

Although the present invention has been described with reference to specific embodiments, it shall be understood that the present invention is not limited to these specific embodiments. Skilled in the art will appreciate that various modifications, substitutions, changes and so on may be made to the present invention. For example, in the above embodiments one step or component may be divided into multiple steps or components; or, on the contrary, a plurality of steps or components in the above embodiments may be realized in one step or one component. All such variations should be within the scope of protection as long as they do not depart from the spirit of the present invention. In addition, the terms as used in the present specification and claims are not limitative, but descriptive. Moreover, according to actual needs, the entire or part of the features described in one specific embodiment can be incorporated into another embodiment.

What is claimed is:

1. An automatic scanning and positioning apparatus for a scout image, the apparatus comprising:

a receiver configured to receive a scout image of a subject obtained through scout scanning with an X-ray computed tomography apparatus;
a processor configured to:
  receive as an input a type of scan to be performed:
  check at least one position in the scout image according to a plurality of information contained in the scout image, wherein the plurality of information comprises gradient information, grayscale information, and position information of a skull of the subject, and the at least one position is selected based on the received type of scan, and
  determine a scanning scope based on the at least one position; and
an executor configured to execute axial scanning with the X-ray computed tomography apparatus to the subject based on the determined scanning scope.

2. The apparatus according to claim 1, wherein the type of scan is a sinuses scan, and the at least one position comprises a frontal sinus position and a nasal end position of the subject, and
wherein the processor comprises:
  a frontal sinus detecting module configured to detect the frontal sinus position and
  a nose detecting module configured to detect the nasal end position.

3. The apparatus according to claim 2, wherein the frontal sinus detecting module uses the gradient information and the grayscale information to obtain the position information, and detects the frontal sinus position by taking the position information as a reference and utilizing the gradient information and the grayscale information.

4. The apparatus according to claim 3, wherein the position information comprises a central point of the skull.

5. The apparatus according to claim 4, wherein circular fitting is conducted to the skull by combining the gradient information and the grayscale information, thereby obtaining the central point.

6. The apparatus according to claim 2, wherein the nose detecting module adopts a multi-resolution and proportion template matching algorithm to detect the nasal end position.

7. The apparatus according to claim 6, wherein the multi-resolution and proportion template matching algorithm is performed according to the following manner:
  generating a plurality of templates by landmarking a nasal region on a plurality of previously existing anteroposterior scout images;
  processing the plurality of templates to N resolution horizontal images; and
  executing a matching treatment by using different search windows of the N resolution horizontal images, and through a correlative matching method, so as to find an optimum match of the scout image.

8. The apparatus according to claim 2, wherein the type of scan is an orbit scan, and the at least one position comprises an orbital position of the subject,
wherein the processor comprises:
  a coarse detecting module configured to detect a coarse orbital position; and
  a precise detecting module configured to precisely detect the orbital position based on the coarse orbital position.

9. The apparatus according to claim 8, wherein the coarse detecting module uses the gradient information and the grayscale information to obtain the position information, and detects an evident partial contour of the orbital position by taking the position information as a reference and utilizing the gradient information, further obtaining an orbital center and an orbital radius.

10. The apparatus according to claim 9, wherein the position information comprises a central point and a skull radius of the skull.

11. The apparatus according to claim 10, wherein circular fitting is conducted to the skull by combining the gradient information and the grayscale information, thereby obtaining the central point and the skull radius.

12. The apparatus according to claim 11, wherein the precise detecting module obtains the precise detection by adopting a texture segmentation method, based on the orbital center, the orbital radius, and the gradient information.

13. The apparatus according to claim 9, wherein the precise detecting module obtains the precise detection by adopting a texture segmentation method, based on the orbital center, the orbital radius, and the gradient information.

* * * * *